United States Patent [19]

Tritsch

[11] 4,034,752

[45] July 12, 1977

[54] DISPOSABLE DIAPER HAVING MULTIPLE TAPE TABS ADHERED TO DIAPER BACKING SHEET

[75] Inventor: Ludwig Tritsch, Wilmette, Ill.

[73] Assignee: Johnson & Johnson, New Brunswick, N.J.

[21] Appl. No.: 665,663

[22] Filed: Mar. 10, 1976

[51] Int. Cl.² .................................. A61F 13/16
[52] U.S. Cl. ............................ 128/184; 128/187
[58] Field of Search .......... 128/287, 284, 290, 156; 24/67 AR, DIG. 11; 248/205 A; 206/231

[56] References Cited

U.S. PATENT DOCUMENTS

| | | | |
|---|---|---|---|
| 3,221,738 | 12/1965 | Ekberg et al. | 128/287 |
| 3,951,149 | 4/1976 | Ness | 128/284 X |
| 3,967,622 | 7/1976 | Cepuritis | 128/287 |

Primary Examiner—Stephen C. Pellegrino

[57] ABSTRACT

A disposable diaper is provided with a release region on the diaper outside surface spaced inwardly from the longitudinal margins of the diaper. At least one tape segment having an adhesive-coated face is releasably parked on the release region, and is completely removable therefrom for securing the diaper about an infant. A plurality of tape segments may be releasably parked on the release region so that after securement the diaper can be removed from the infant and thereafter refastened thereon by means of subsequent tape segments. One or more release regions may be provided. Preferably, two release regions are provided spaced inwardly from opposite longitudinal margins of the diaper, with at least two tape segmens being releasably parked on each release region.

10 Claims, 6 Drawing Figures

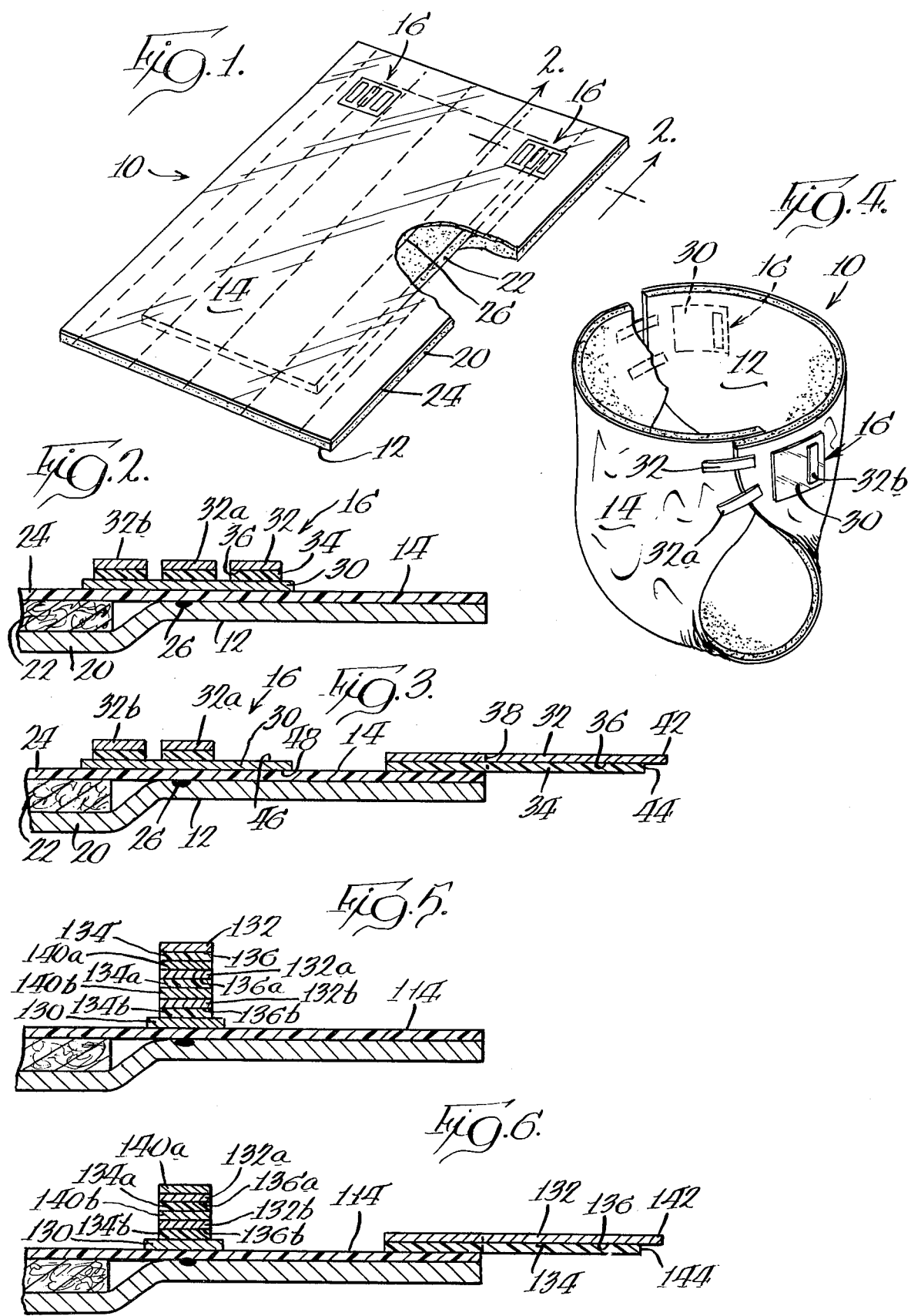

DISPOSABLE DIAPER HAVING MULTIPLE TAPE TABS ADHERED TO DIAPER BACKING SHEET

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a facing material to be brought into contact with the infant's skin, an absorptive layer of high liquid-holding capacity, and a moisture-impervious backing layer, generally made of a plastic film such as a polyethylene film. Typical disposable structures are shown in U.S. Pat. No. 3,612,055 to Mesek et al. and in U.S. Pat. No. Re. 26,151 to Duncan et al.

As may be seen from the above-cited patents, it has been desired to obviate the problems that are inherent in closure systems utilizing extraneous fasteners such as safety pins, snaps and zippers. To this end, adhesive closure systems have presented acceptable solutions.

One of the most convenient adhesive systems that has been developed to date is the system, shown in the above-cited patents, in which adhesive tabs have fixed ends permanently adhered to the backing sheet at opposite sides of the diaper at one end thereof. Free exposed ends of these adhesive tabs are utilized to effect diaper securement and are protected by cover strips that are readily separable from the exposed adhesive surfaces of the tabs. Disposable diapers using an adhesive closure system of this general type have the disadvantage in that the consumer has to dispose of the cover strips when they are separated from the adhesive strips. This is an inconvenience to the consumer who is placing the diaper on an infant.

An illustrative prior art adhesive system having cover strips permanently attached to the diaper is disclosed in U.S. Pat. No. 3,646,937 to Gellert. The Gellert arrangement has the disadvantage of having the release film on the inside of the diaper, where it can possibly come in contact with an infant's tender skin. Additional disadvantages are the complexities and expense which are added to the manufacturing process by requiring each adhesive closure to be manipulated on the front side, around the edge, and on to the back side of the diaper, instead of handling it on one side only. The closure system illustrated in the Gellert patent also makes it somewhat difficult to secure the diaper around an infant, in that it requires the use of both hands to remove the releasable end of the adhesive tape.

The prior art tab systems have further disadvantages. The permanent attachment of one end of the tab to the diaper limits the ability of the user to place the tab on the diaper to obtain the best fit on each individual baby. By "pre-locating" the placement of one end of the tab on the diaper, the degree of freedom in tape tab placement is significantly limited.

A further problem resulting from permanently attaching one end of the tab on the diaper before using the diaper is tape tab pull-out. This results when a user is fitting the diaper on an infant and pulls on the tape tab with too much force, thereby applying excessive tension to the diaper, which causes diaper rupture and the separation of the tab from the diaper.

SUMMARY OF THE INVENTION

In accordance with the present invention, an adhesive tab fastener for a disposable diaper includes a release region on the diaper outside surface and spaced inwardly from the longitudinal margins of the diaper, and at least one tape segment which is releasably parked on the release region. The tape segment has a pressure-sensitive adhesive coating on one face thereof which coating is in releasable contact with the release region. The tape segment is readily removable from the release region to make the entire adhesive area of the adhesive-coated tape segment available for securing the diaper about an infant.

If desired, a plurality of tape segments may be releasably parked on the release region so that once a diaper is secured about an infant, the diaper can be opened or removed from the infant one or more times and thereafter refastened by means of tape segment or segments still parked on the release region. Where a plurality of tape segments are provided, a user can also employ two or more tape segments on each side of the applied diaper to snugly fit the diaper about the infant. A tight fit can thereby be attained, especially in the infant's thigh region, which region has heretofore been difficult if not impossible to fit using prior art systems. Each tape segment can be releasably parked directly on the same release region, or the tape segments can be backsized with a release composition and stacked, with the first tape segment releasably parked on the release region anchored to the diaper backing sheet, and each subsequent tape segment being releasably parked on the release region carried by the underlying tape segment.

One or more release regions can be utilized. Preferably, at least two release regions may be provided on a diaper backing sheet, spaced inwardly from opposite longitudinal margins of the diaper, and having at least two tape segments releasably parked on each release region.

The tab configuration of the present invention obviates the need for an extraneous cover strip for each tab since the release region is permanently attached to the diaper outside surface. The present invention provides a further advantage in that the release region remains on the diaper outside surface where it is out of contact with an infant's tender skin. Moreover, the tabs themselves remain flat against the diaper when parked on the release region and do not interfere with the diaper manufacturing machinery and the subsequent packaging operations.

BRIEF DESCRIPTION OF THE DRAWINGS

FIG. 1 is a perspective view of an open unfolded disposable diaper in accordance with one embodiment of the invention, parts of the diaper being broken away to show interior construction;

FIG. 2 is an enlarged fragmentary cross-sectional view taken along plane 2—2 in FIG. 1;

FIG. 3 is a fragmentary cross-sectional view showing a tab fastener in the working position and a pair of tab fasteners in the parked position;

FIG. 4 is a perspective view of the diaper of FIG. 1 in a configuration assumed by the diaper when placed about an infant and providing an improved fit;

FIG. 5 is fragmentary cross-sectional view similar to FIG. 2 and showing an alternate embodiment of the invention with a plurality of tab fasteners stacked in a storage position; and FIG. 6 is a fragmentary cross-sectional view showing the embodiment of FIG. 5 with one tab fastener in a working position and the remainder of tab fasteners in the storage position.

DESCRIPTION OF THE PREFERRED EMBODIMENTS

In the following description, two digit numerals are used to refer to the embodiment illustrated in FIGS. 1–4, and three digit numerals in the one hundred series are used to refer to the embodiment illustrated in FIGS. 5 and 6. The same last two digits in each numeral designate similar structural elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tabs such as tab 16 are attached to diaper 10 for securing diaper 10 about an infant.

Referring to FIGS. 1 and 4, diaper 10 comprises a moisture-retaining layer made of moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 usually is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to backing sheet 24 by means of adhesive beads 26, glue spots, or in any other convenient manner. For example, if backing sheet 24 is made of a thermoplastic material, facing sheet 20 and pad 22 can be attached thereto by heat bonding.

As illustrated in FIGS. 1–4, release region 30 is provided on the diaper outside surface and is spaced inwardly from a longitudinal margin of the diaper. At least one tape segment 32 having an adhesive coating 34 on inner face 36 thereof is releasably parked on release region 30 so that adhesive coating 34 is releasably held on release region 30. As shown in FIGS. 2 and 3, tape segment 32 is removable from release region 30 to make the entire surface of adhesive coating 34 available for securing the diaper about an infant by attaching one end of the tape segment to one corner of the diaper outside surface 14 adjacent a longitudinal margin of the diaper, and attaching the opposite end of the tape segment to an opposite corner of the diaper.

Where only a single release region 30 is provided on diaper outside surface 14, at least two tape segments 32 and 32a are releasably parked on the release region. Preferably, at least two release regions 30 are provided and are spaced inwardly from opposite longitudinal margins of the diaper, as shown in FIGS. 1 and 4. It is desirable to position release regions 30 near opposite corners of the diaper at the same transverse end thereof. A plurality of tape segments can be releasably parked on each of the release regions 30. To secure the diaper initially, a first tape segment 32 from the plurality can be removed from each release region. Each tape segment may also be provided with a line of weakening 38 (FIG. 3) extending transversely across the tape segment to facilitate tearing of the tape segment when it is desired to open the diaper or to remove the diaper from the infant. To refasten the diaper about the infant, second tape segment 32a from the parked plurality of segments can be removed from each release region 30 for attachment to diaper outside surface 14 adjacent a longitudinal margin of the diaper. Where each release region 30 has three or more tape segments releasably parked thereon, subsequent tape segments 32b can be removed from release region 30 as needed for further refastening of the diaper or to improve the fit of an already applied diaper.

Whether there is a single release region or two or more release regions on diaper outside surface 14, a plurality of tape segments may be releasably parked on each release region so that a user can simultaneously employ two or more tape segments at each end of the diaper to snugly position the diaper about the infant, as shown in FIG. 4. A tight fit of the diaper about the thigh region of the infant can thereby be attained.

In the embodiment illustrated in FIGS. 1–4, tape segments 32, 32a and 32b are all releasably parked on release region 30 with adhesive coating 34 on inner face 36 of each tape segment being juxtaposed to release region 30. Each tape segment is thereby releasably attached directly to release region 30.

An alternate embodiment, having stacked tape segments, is illustrated in FIGS. 5 and 6. Tape segment 132b has adhesive coating 134b on inner face 136b thereof, and is releasably attached directly to release region 130 on diaper outside surface 114. Tape segment 132b also has release coating 140b on the back side, i.e., the unattached face, thereof. Additional tape segment 132a is releasably stacked on top of the directly attached tape segment 132b. Tape segment 132a has adhesive coating 134a on inner face 136a thereof, adhesive coating 134a being in releasable attachment with release coating 140b carried by tape segment 132b. Similarly, additional tape segments can be releasably stacked on top of the underlying tape segment. For example, tape segment 132 (FIG. 5) has an adhesive coating 134 on inner face 136 thereof, and is releasably parked on release coating 140a carried on the opposite face of tape segment 132a. The uppermost or outermost tape segment 132 need not have a release coating on the unattached face thereof.

Tape segment 132 is removable from the underlying release-coated tape segment 132a to secure the diaper about an infant initially. The diaper can be removed from the infant by removing or severing tape segment 132, and thereafter refastened on the infant by lifting tape segment 132a away from the underlying release-coated tape segment 132b. Similarly, subsequent tape segments 132b are removable for further refastening the diaper.

In both of the aforesaid embodiments, it is desirable to provide a gripping means to facilitate grasping the tape segment for separating the tape segment from the underlying release region or release coating preparatory to fastening the diaper about the infant. Thus, as shown in FIG. 3, one end of tape segment 32 can include projecting portion 42 which extends beyond outermost edge 44 of adhesive coating 34 and provides a gripping means.

To facilitate gripping the tape segments from release region 30 in preparation for fastening the diaper about an infant, preferably release region 30 has a release surface area which is greater than the combined adhesive area on the tape segments which are parked thereon, as shown in FIG. 1.

Adhesive tabs suitable for the purposes of the present invention can be made from a wide variety of materials, provided that such materials are sufficiently flexible. Particularly preferred materials for this purpose are polyolefin webs such as polyethylene sheet, polypropylene sheet, and the like.

The pressure-sensitive adhesive coatings such as adhesive coating 34 are provided by applying a coating of a pressure-sensitive adhesive composition known in the art to the appropriate surface of tape segment 32. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of tacky acrylic polymers or copolymers, and the like.

The release regions 30 may comprise ribbon segments or release strips carried on diaper outside surface 14 and provided with a release coated face 46 (FIG. 3) which provides the release region, and an adhesive coating on opposite face 48 by means of which the release strip is anchored to backing sheet 24. Alternatively, release region 30 may comprise a release coating, such as a silicone release compound, or the like, which is substantially coextensive with the adhesive-coated tape segments. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,544 to Dickard.

Several different types of facing material may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as non-woven isotropic web, or the like. In all of the aforementioned facing materials, the material should be relatively hydrophobic so as to retard wicking within the facing layer.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive tab fasteners are then prepared for use by grasping one of the tape segments to separate the individual tape segment from the underlying release region 30 or release coating 140 to which it is releasably attached, attaching one end of the tape segment to one corner of the diaper outside surface adjacent a longitudinal margin of the diaper, and then securing the diaper in the desired position by simply urging the pressure-sensitive adhesive surface on the other end of the tape segment in contact with the adjacent outer surface of the opposite corner of the diaper. A second tape fastener is applied to each side after the diaper has been adjusted to the desired fit in the thigh regions of the infant. The applied diaper assumes a configuration such as shown in FIG. 4, and can be removed from the infant and thereafter refastened about the infant as described hereinabove.

In the illustrations described hereinabove, the tab fastener system of this invention has been utilized as the sole securement means for a disposable diaper. It should be understood, however, that the fastener means of the present invention can also be used in combination with other known diaper tab fastener systems so as to provide repositionability, enhanced fit, or other advantages.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and adhesive tab fastener means comprising:
   a release region on the diaper outside surface spaced inwardly from the margins of said diaper;
   at least one tape segment releasably parked on said release region, said tape segment having a pressure-sensitive adhesive coating on one face thereof which is releasably attached to said release region, each tape segment being positioned on said release region in its entirety inwardly from the margins of said diaper;
   each said tape segment being removable from said release region and from said diaper in its entirety to make the entire adhesive-coated area thereof available for attachment to any desired position on said diaper for securing said diaper about an infant.

2. The disposable diaper as defined in claim 1 wherein at least two relase regions are provided and are spaced inwardly from opposite longitudinal margins of said diaper.

3. The disposable diaper as defined in claim 1 wherein two release regions are provided near opposite corners of said diaper at the same transverse end thereof, and wherein at least two tape segments are releasably parked on each release region.

4. The disposable diaper as defined in claim 1 wherein at least one tape segment having two opposed faces is attached at one face directly to said release region and has a release coating on the unattached face thereof, and wherein at least one additional tape segment is releasably stacked on top of said directly attached tape segment.

5. The disposable diaper as defined in claim 4 wherein a portion of each said tape segment projects beyond the outermost edge of said adhesive coating carried thereon, whereby said projecting portion provides a gripping means for separating said tape segment from an underlying release surface preparatory to fastening said diaper about said infant.

6. The disposable diaper as defined in claim 4 wherein two release regions are provided near opposite corners of said diaper at the same transverse end thereof, and wherein at least one stack of tape segments is releasably parked on each of said release regions.

7. The disposable diaper as defined in claim 1 wherein a portion of said tape segment projects beyond the outermost edge of said adhesive coating carried thereon, whereby said projecting portion provides a gripping means for separating said tape segment from said release region preparatory to fastening said diaper about said infant.

8. The disposable diaper as defined in claim 1 wherein said release region has a release surface area which is greater than the combined adhesive area on said tape segments parked thereon to facilitate gripping said tape segments for separation from said release region in preparation for fastening said diaper about said infant.

9. A disposable diaper having a facing sheet defining a diaper inside surface for direction toward an infant, a moisture-impervious backing sheet substantially coextensive with said facing sheet and defining a diaper outside surface, an aborbent panel positioned between said facing and said backing sheet, and adhesive tab fastener means comprising:
   a release region on the diaper outside surface spaced inwardly from a longitudinal margin of said diaper;
   a plurality of tape segments which are releasably parked on said release region, said tape segment having a pressure-sensitive adhesive coating on one face thereof which is releasably attached to said release region;
   a first tape segment from said plurality being removable from said release region to make the entire adhesive area of said adhesive-coated tape segment available for securing said diaper about an infant initially, and subsequent tape segments of said plurality being removable from said release region to refasten said diaper about the infant.

10. The disposable diaper as defined in claim 9 wherein at least two tape segments are releasably parked on said release region.

* * * * *